(12) United States Patent
Ott-Dombrowski et al.

(10) Patent No.: US 11,104,630 B2
(45) Date of Patent: Aug. 31, 2021

(54) SYNTHESIS OF MONO-CHLORINATED ACETOPHENONE

(71) Applicant: SIEGFRIED AG, Zofingen (CH)

(72) Inventors: Silvia Ott-Dombrowski, Petershagen (DE); Henning Rüter, Bad Essen (DE); Reto Ulrich, Zofingen (CH); Franz Zumpe, Rheinfelden (CH)

(73) Assignee: SIEGFRIED AG, Zofingen (CH)

( * ) Notice: Subject to any disclaimer, the term of this patent is extended or adjusted under 35 U.S.C. 154(b) by 0 days.

(21) Appl. No.: 16/954,822

(22) PCT Filed: Dec. 14, 2018

(86) PCT No.: PCT/EP2018/084908
§ 371 (c)(1),
(2) Date: Jun. 17, 2020

(87) PCT Pub. No.: WO2019/121379
PCT Pub. Date: Jun. 27, 2019

(65) Prior Publication Data
US 2021/0107853 A1    Apr. 15, 2021

(30) Foreign Application Priority Data

Dec. 18, 2017 (EP) ..................................... 17208144

(51) Int. Cl.
*C07C 45/63* (2006.01)
*C07C 213/04* (2006.01)
*C07C 49/80* (2006.01)
*C07C 215/60* (2006.01)

(52) U.S. Cl.
CPC ............. *C07C 45/63* (2013.01); *C07C 213/04* (2013.01); *C07C 49/80* (2013.01); *C07C 215/60* (2013.01)

(58) Field of Classification Search
CPC .............................. C07C 45/63; C07C 213/04
See application file for complete search history.

(56) References Cited

U.S. PATENT DOCUMENTS 7,385,087 B2 *  6/2008  Altmayer .............. C07C 319/14
                                                              568/43
8,617,854 B2 * 12/2013  Breuer ...................... C12P 7/22
                                                             435/128

FOREIGN PATENT DOCUMENTS

DE         10309645 A1   9/2004
WO       2010031776 A2   3/2010

OTHER PUBLICATIONS

International Search Report and Written Opinion dated Feb. 12, 2019 for corresponding PCT Application No. PCT/EP2018/084908.
European Search Report dated May 14, 2018 for corresponding European Application No. 17208144.0.

* cited by examiner

*Primary Examiner* — Sikarl A Witherspoon
(74) *Attorney, Agent, or Firm* — Polsinelli PC

(57) ABSTRACT

The present invention relates to the improved synthesis of chlorinated acetophenones (CAP) of formula (I). Particularly, the invention shows a way how to reduce the use of chlorinated solvents and the formation of chlorinated volatile by-products in the synthesis.

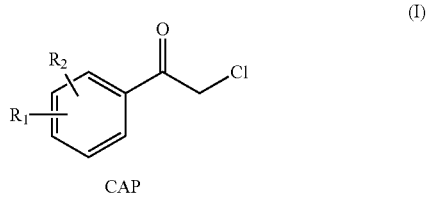

CAP

19 Claims, No Drawings

SYNTHESIS OF MONO-CHLORINATED ACETOPHENONE

CROSS-REFERENCE TO RELATED APPLICATIONS

This application is a national stage application (under 35 U.S.C. § 371) of PCT/EP2018/084908, filed Dec. 14, 2018, which claims benefit of European Application No. 17208144.0, filed Dec. 18, 2017, which are incorporated herein by reference in their entireties.

FIELD OF THE INVENTION

The present invention relates to the improved synthesis of chlorinated acetophenones (CAP) of formula (I).

FIG. 1

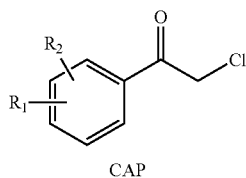

CAP

Particularly, the invention shows a way how to reduce the use of chlorinated solvents and chlorinated volatile by-products in the synthesis.

$R_1$ and $R_2$ may be independently H or OH or a substituted C1-C4 alkyl.

TECHNICAL BACKGROUND

CAPs are widely used in organic synthesis as intermediates for the manufacture of active pharmaceutical ingredients (APIs):

The preparation of alpha-chloro aryl ketones (formula I) has been a task for several decades. (see Swamy et al, Chem. Lett. 2012, 41, 432-434). Since 1963, when it was claimed that for the alpha-chlorination of aryl ketones the only way is to use sulfuryl chloride, this reaction was solely performed in chlorinated solvents.

The preparation of chlorinated acetophenons is usually achieved by chlorination of the corresponding substituted acetophenone (II) with sulfuryl chloride.

FIG. 3

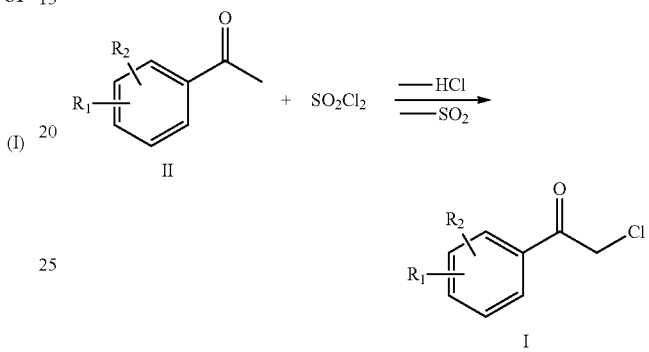

In WO2010031776 it is described that 3-hydroxyacetophenon may, as an example for a substituted acetophenone, be chlorinated with sulfuryl chloride in the presence of 1-10 mol equivalents of an alcohol. It has been found as advantageous to use dichloromethane (methylene chloride, DCM) as solvent for this reaction.

Numbering of substances of formula I and II is conducted according to the following scheme:

FIG. 2

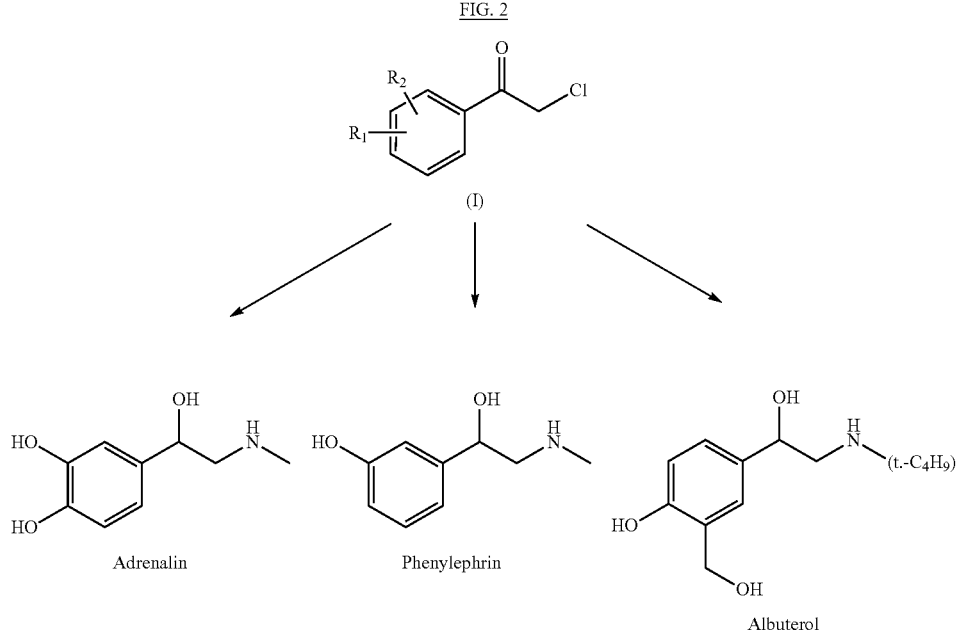

Adrenalin     Phenylephrin     Albuterol

FIG. 4

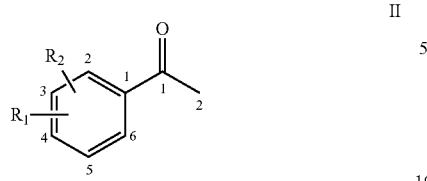

Wyman et al. have tried benzene for a chlorination reaction, but with no success. (J. Org. Chem., 1964, 29 (7), pp 1956-1960)

Also Masilamani and Rogic (J. Org. Chem. 1981, 46, 4486-4489) explain that alpha-mono-chlorination of ketones may be achieved in the presence of a nucleophile (Nu, such as methanol) via the following steps:

FIG. 5

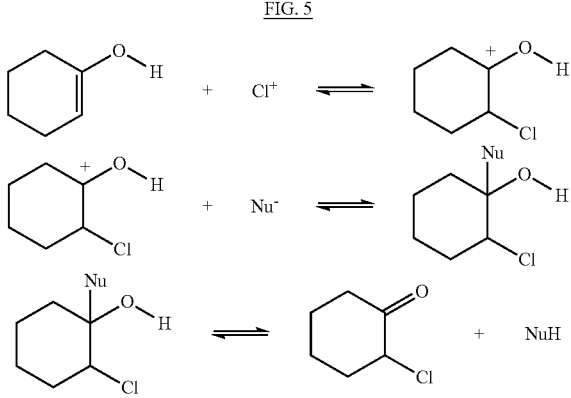

However, Masilamani et al. also show that core-substitutions may occur if methanol is used with aromatic systems in dichloromethane.

FIG. 6

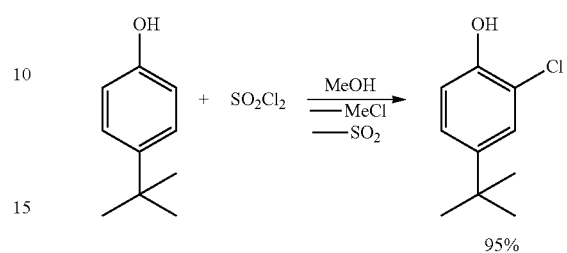

Also Guy et all report that sulfuryl chloride may chlorinate activated aromatic rings. They propose to achieve alpha-mono-chlorination with hexachloro-2,4-cyclohexadienone. (Synthesis, 1982, Vol. 12, pp 1018-1020).

Wyman at al. have reported that the dichloro-compound is also present in the reaction product of sulfuryl chloride and phenylacetone. (J. Org. Chem., 1964, 29 (7), pp 1956-1960) The amount of about 3% (HPLC area-%) is corresponding to our results with 3-hydroxyacetophenone.

Table 1 shows the impurities formed in side reactions when using sulfuryl chloride as chlorinating agent for acetophenone. The table also shows the amount of the side product (as HPLC area-%) when using the state of the art process in dichloromethane. Some of these impurities are hard to separate from the product.

TABLE 1

| | | |
|---|---|---|
| 2-Chloro-1-(2-chloro-3-hydroxy-phenyl)-ethanone (Core 1) | | 1 to 2 Area % |
| 2-Chloro-1-(3-hydroxy-4-chloro-phenyl)-ethanone (Core 2) | | 1 to 2 Area % |
| 2-Chloro-1-(2-chloro-5-hydroxy-phenyl)-ethanone (Core 3) | | 1 to 3 Area % |
| 2,2-Dichloro-1-(3-hydroxy-phenyl)-ethanol (Sidechain) | | 3 to 7 Area % |

Masilamani et al. have thereafter proposed a mechanism that incorporates an alcohol as a nucleophile (see above, J. Org. Chem., 1981, 46 (22), pp 4486-4489). They also show several attempts with dichloro-products as side products, and suggested dichloromethane as the solvent of choice. The same authors also describe in U.S. Pat. No. 4,310,702 that different moderators may be used, methanol being one of them.

Environmental aspects of industrial applications gain more and more weight in economic decisions. This is underlined for example with the regulations for avoiding chlorinated waste material during chemical synthesis (see "31. Verordnung zur Durchführung des Bundes-Immissionsschutzgesetzes (Verordnung zur Begrenzung der Emissionen flüchtiger organischer Verbindungen bei der Verwendung organischer Lösemittel in bestimmten Anlagen) (31. BImSchV)"). Anyone who is using chlorinated solvents is obliged to exchange these solvents wherever possible.

We have therefore given ourselves the task to find a new way of forming chlorinated acetophenones whilst avoiding chlorinated solvents and also avoiding the formation of volatile chlorinated by-products.

Approaches with different chlorinating agents show that the task is not solved properly. See Swamy et al. in Chemistry Letters, 2012, Vol. 41, Issue 4, pp 432-434 and Guy et al. in Synthesis, 1982, Vol. 12, pp 1018-1020.

Masilamani et al. as well as Swamy et al. have published in the publications mentioned above the use and influence of different solvents in the monochlorination of acetophenones.

SUMMARY OF THE INVENTION

We have now surprisingly found that the chlorination of acetophenon derivatives is very advantageous in the presence of toluene. Toluene is not only a good alternative to dichloromethane. It also shows unexpected improvement with regard to impurity profile and Quality.

DESCRIPTION OF THE INVENTION

In this invention, 3-hydroxy-acetophenon (HAP) stands exemplarily for different substituted acetophenones. However, there seems no obvious reason, why this reaction should not also work for other substituted acetophenones. There are no well-founded reasons for believing that the skilled person would be unable, on the basis of the information given in the application, to extend the particular teaching of the description to other substrates as described in FIG. 7 wherein $R_1$ and $R_2$ may be independently H or OH or a substituted C1-C4 alkyl.

by using routine methods of experimentation.

FIG. 7

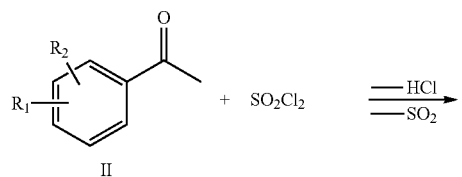

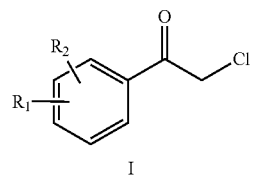

In order to exchange the chlorinated solvent from the reaction, different solvents where tested for suitability for the reaction of sulfuryl chloride and 3-hydroxy-acetophenon.

As solvents of choice, the solvents that had been used in the literature for chlorination with sulfuryl chloride were tested.

Masilamani et al propose:

Diethylether (Ether), THF, p-dioxane, tetraglyme, $SO_2$

Swamy et al propose the following solvents:

Methanol, Ethanol, Acetonitrile, Acetone, Ethyl acetate

In a first try the compatibility between sulfuryl chloride and the solvent was tested. See Table 9 in the annex.

All solutions except sulfuryl chloride in dichloromethane turned yellowish after a few minutes, indicating that a reaction between the sulfuryl chloride and the solvent or decomposition of sulfuryl chloride took place. With some of the solvents even a rising temperature and/or evolution of gas was observed. This underlines why chlorinated hydrocarbons are used as solvents of choice for reactions with sulfuryl chloride.

The solubility of the starting material in the solvents with the lowest reactivity towards the sulfuryl chloride was also tested. A value of less than 50 was regarded as acceptable because industrially applicable.

Table 2 shows the solubility in ml solvent to be used for one gram of HAP:

TABLE 2

| Example | Solvent | Solvent in ml per g HAP | Other remarks |
|---|---|---|---|
| 2.1 | DCM | 22 | DCM potentially carcinogenic |
| 2.2 | Tetraglyme | 9 | |
| 2.3 | Methanol | 10 | |
| 2.4 | Ethanol | 20 | |
| 2.5 | Acetone | 46 | |
| 2.6 | Acetonitrile | 6 | |

All solvents seemed to be usable with regard to the solubility of the starting material.

Table 3 shows the reaction of HAC in the solvents of choice. Solvents that seem to react with sulfuryl chloride were not tested:

TABLE 3

| Example | Solvent | Moderator | 3-HAP | HCAP | Core1 | Core2 | Core3 | Sidechain | remark |
|---|---|---|---|---|---|---|---|---|---|
| 4.1 | Tetraglyme | MeOH | 30.0 | 62.4 | 0.2 | 0.7 | 0.5 | 5.7 | |
| 4.2 | Ether | MeOH | 35.0 | 52.1 | 1.8 | 0.5 | 1.5 | 2.3 | |
| 4.3 | Acetonitrile | MeOH | 62.5 | 23.2 | 1.7 | 1.9 | 0.3 | 6.5 | |

None of the selected solvents gave a satisfying conversion rate of hydroxyacetophenone to the corresponding monochlorinated product.

Thus, in a second step also solvents have been tested that had not been used for the mono-chlorination of phenylacetones before. Table 4 shows the solubility of the starting material in these solvents.

TABLE 4

| Example | Solvent | Solvent in ml per g HAP | Other remarks |
|---|---|---|---|
| 2.7 | MTBE | 9 | |
| 2.8 | Ether | 8 | |
| 2.9 | Cyclohexane | >200 | |
| 2.10 | n-Heptane | 20 | |
| 2.11 | Toluene | 156 | Benzyl chloride carcinogenic, also possibility of core substitutions with $SO_2Cl_2$ |
| 2.12 | n-Hexane | 23 | |

According to this evaluation, toluene and cyclohexane could be excluded as first choice solvents because of the low solubility of the starting material in the solvent. Furthermore, it was expected that toluene would also be chlorinated by sulfuryl chloride, since toluene can be regarded as activated aromatic ring according to Guy et al. See above. See also example in FIG. 6.

MTBE, ether, n-heptane and n-hexane did not show acceptable results. However, although cyclohexane and toluene had been excluded already and should not have been used for the reaction, cyclohexane and toluene were used in the tests and surprisingly, the conversion rate was very good for the reaction in toluene.

However, for these solvents the reaction was conducted in a suspension rather than in a solution.

Surprisingly, the use of toluene as solvent was very successful in the reaction of hydroxyacetophenone with sulfuryl chloride. No reaction of toluene with sulfuryl chloride was observed, although the state of the art would indicate this. (see also K. H. Lee in Tetrahedron, 25, 4363, 1969). Furthermore, as an unexpected advantage, in the isolated product the impurity that occurs as a result of sidechain double chlorination is extremely reduced in the presence of toluene.

With toluene as the solvent it could thus be prevented to use a chlorinated solvent like DCM in the reaction.

The use of the new solvent helps to avoid chlorinated hydrocarbons in industrial waste material. It could even be shown that, as an unexpected advantage, the products of core substitutions and double chlorination on the side chain could be reduced in the isolated product.

Reaction with the Use of Different Moderators

During the reaction of sulfuryl chloride with the moderator R—OH, alkyl halides like R—Cl are formed in a side reaction with sulfuryl chloride (see FIG. 8). Also Masilamani et al. state that: "Sulfuryl chloride reacts vigorously with methanol at room temperature to give methane sulfuryl chloride, HCl, methyl chloride, and dimethyl sulfate"

TABLE 5

| Example | Solvent | Moderator | 3-HAP | HCAP | Core1 | Core2 | Core3 | Sidechain | remark |
|---|---|---|---|---|---|---|---|---|---|
| 4.4 | MTBE | MeOH | 40.0 | 60.2 | 0.0 | 0.5 | 0.3 | 3.7 | |
| 4.5 | Ether | MeOH | 31.0 | 57.0 | 1.8 | 0.5 | 1.5 | 2.3 | |
| 4.6 | n-Heptane | MeOH | 31.4 | 42.3 | 1.2 | 0.4 | 0.4 | 0.9 | Many other prod. |
| 4.7 | n-Hexane | MeOH | 14.7 | 69.0 | 0.7 | 0.5 | 1.0 | 5.1 | Many other prod. |
| 4.8 | Cyclohexane* | MeOH | 46.1 | 52.3 | 1.0 | 0.4 | 0.4 | 0.9 | |
| 4.9 | Toluene* | MeOH | 1.2 | 82.5 | 0.0 | 0.4 | 0.4 | 0.9 | |

*starting material is not dissolved completely

FIG. 8

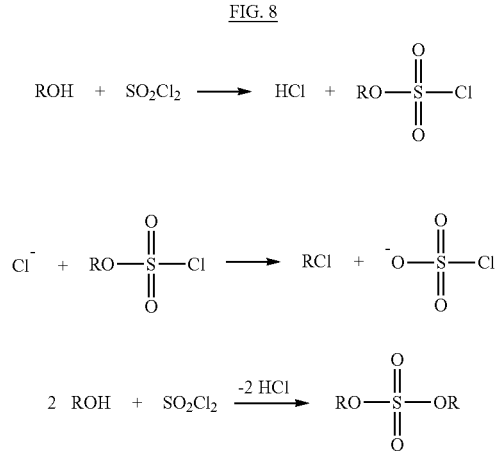

Therefore, according to the state of the art an excess of moderator is necessary to have enough alcohol for the side reactions.

Nevertheless, in the process of reducing the chlorinated hydrocarbons we have also investigated to exclude or reduce the chlorinated hydrocarbon formed during the reaction.

In a first step, the influence of the moderator to conversion rate and side products was investigated.

The following alcohols have been taken into account for this task: Methanol, Ethanol, 1-Propanol, 1-Butanol

TABLE 6

| Example | Solvent (ml per g HAP) | Modulator (ml per g HAP) | 3-HAP | HCAP | Core1 | Core2 | Core3 | Side-chain | remark |
|---|---|---|---|---|---|---|---|---|---|
| 4.13 | DCM (3) | MeOH (2) | 0.0 | 90.2 | 1.3 | 1.5 | 2.4 | 3.7 | Comparative example |
| 4.14 | DCM (3) | 1-Propanol (1) | 0.0 | 87.0 | 1.7 | 0.6 | 2.5 | 7.3 | Comparative example |
| 4.15 | Toluene (6) | Methanol (2) | 1.2 | 82.5 | 0.0 | 0.4 | 0.4 | 0.9 | |
| 4.16 | Toluene (4.5) | Ethanol (6) | 1.5 | 82.3 | 0.0 | 0.4 | 0.4 | 0.9 | |
| 4.17 | Toluene (6) | 1-Propanol (1.5) | 2.6 | 89.0 | 0.7 | 0.5 | 1.0 | 2.1 | |
| 4.18 | Toluene (6) | 1-Butanol (1) | 2.8 | 91.1 | 0.4 | 0.4 | 0.5 | 1.6 | |

The results show that with toluene as the solvent, a variety of aliphatic alcohols may be used as moderators for the reaction.

The HPLC-Results of HCAP are between 82.3% and 91.1%.

1-Butanol seemed to give the best result regarding the conversion rate with regard to the product (91.1%)

In order to further improve the reaction, the inventors started to investigate the reaction with the moderator that gives the highest conversion rate.

1-Butanol was taken for these investigations. See experimental part for full results

TABLE 7

| Entry | Solvent [vol] | Modulator [vol] | 3-HAP | HCAP | Core1 | Core2 | Core3 | Side-chain | remark |
|---|---|---|---|---|---|---|---|---|---|
| 5.1 | Toluene (6) | 1-Butanol (1) | 2.8 | 91.1 | 0.4 | 0.4 | 0.5 | 1.6 | |
| 5.2 | Toluene (6) | 1-Butanol (2) | 2.1 | 90.8 | 0.3 | 0.3 | 0.4 | 1.7 | |
| 5.3 | Toluene (4) | 1-Butanol (2) | 2.1 | 90.8 | 0.3 | 0.3 | 0.5 | 1.7 | |
| 5.4 | Toluene (2) | 1-Butanol (2) | 1.7 | 97.6 | 0.2 | 0.3 | 0.2 | 0.2 | |
| 5.5 | Toluene (2) | 1-Butanol (2) | 7.1 | 66.3 | 0.4 | 0.3 | 0.6 | 0.7 | 10-15° C. |
| 5.6 | Toluene (2) | 1-Butanol (2) | 3.4 | 87.8 | 1.0 | 0.7 | 1.0 | 0.8 | Approx. 30° C. |
| 5.7 | Toluene (2) | 1-Butanol (2) | 1.0 | 75.2 | 1.5 | 1.6 | 1.6 | 3.6 | Approx. 60° C. |

During these investigations it could be shown that the outcome of the reaction is not strongly depending on the right selection of temperature and amount of solvent and amount of sulfuryl chloride used.

The reaction may be performed at temperatures between 10° C. and 60° C. with acceptable yield. However, sidechain chlorination and core substitution are increased at higher temperatures.

Reduction of the Amount of Aliphatic Alcohol

After studying the state of the art, it is obvious that at least an equimolar ratio of aliphatic alcohol is necessary to perform the reaction. (see FIG. 5). With regard to the side reactions that occur between sulfuryl chloride and aliphatic alcohol, one would assume that even more aliphatic alcohol is needed for the reaction, since part of the aliphatic alcohol is used up by these side reactions. (FIG. 8)

Despite the proposed mechanism and also considering the side reactions of sulfuryl chloride, which would anticipate the need of a molar excess of aliphatic alcohols, the inventors tried against the teaching of the prior art to reduce the amount of the moderator in the reaction.

In a further study, therefore the influence of the amount of aliphatic alcohol in the reaction has been investigated and it was tried to reduce the amount of the aliphatic alcohol. See Table 10 for this study.

It could be shown that the reduction of n-Butanol to equimolar amounts did not negatively influence the impurity profile or the conversion rate of the reaction. A preferred embodiment of the invention is therefore to use not more than one equivalent aliphatic alcohol in the reaction.

Even more surprising is the fact that, if the alcohol is used in lower than equimolar amounts, the yield of the isolated product was increased.

Also, in the isolated and dried product, the impurity profile was surprisingly better when reduced amounts of alcohol are used.

The results also teach that methanol showed under these reaction conditions good conversion rate, impurity profile and isolated yield. See Table 11 Therefore in a preferred embodiment of the invention the alcohol is used in a molar ratio of less than 1 with regard to the acetophenone derivative.

In a more preferred embodiment of the invention the alcohol is used in a molar ratio of between 0.05 and less than 1 with regard to the acetophenone derivative.

Best results have been achieved with alcohol amount in a molar ratio of between 0.1 and 0.3 with regard to the acetophenone derivative.

In summary, it could be shown that when selecting toluene as solvent for the reaction, less than 1 equivalents of moderator are needed for the reaction to work properly.

This reduces furthermore the formation of chlorinated side products from the reaction of sulfuryl chloride and the aliphatic alcohol.

It was also tried to perform the reaction with no moderator, but this was not successful.

The reaction may be performed at temperatures between 10° C. and 60° C. with acceptable yield.

Temperatures of 20° C. and more have shown better results with regard to conversion rate and isolated yield. In a preferred embodiment of the invention, the temperature of the reaction is 20° C. or more.

The ideal temperature depends on the moderator used. For methanol for example, the ideal temperature is 38-42° C. For Butanol as moderator, the ideal temperature is at about 30° C.

In a preferred embodiment the reaction temperature is kept at 38–42° C. for the use of methanol as moderator.

The product may be used directly after filtration or may be further purified by standard techniques like chromatographic methods or crystallization.

Chromatography might be performed on normal phase or reverse phase chromatographic systems. Solvents for the mobile phase are for example: acetonitrile, DCM, methanol, acetone, aliphatic hydrocarbons and other standard solvents. Acetic acid or phosphoric acid may be used to set the pH of the mobile phase. Crystallization may be performed with any of the solvents as described within this application. Reduction of temperature may induce crystallization. Crystallization may also be induced by seeding of the solution.

DETAILED DESCRIPTION OF THE INVENTION

According to the above mentioned reasons, the invention discloses a process for the preparation of monochlorinated substituted acetophenones, from the corresponding acetophenone, preferably 3-hydroxyacetophenone, in the presence of toluene as depicted in FIG. 9, wherein $R_1$ and $R_2$ may be independently H or OH or a substituted C1-C4 alkyl

FIG. 9

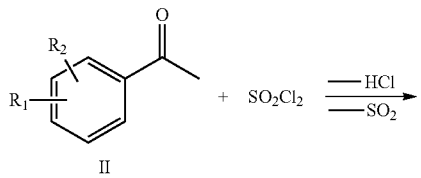

II

TABLE 8

| Example. | Remarks | SO$_2$Cl$_2$ [eq.] | Volumes (dil. of SO$_2$Cl$_2$) [g] | Butanol [eq.] | Toluene [Vol] | HPLC-results [a %]* | | | | | | | yield [%] |
|---|---|---|---|---|---|---|---|---|---|---|---|---|---|
| | | | | | | 3-HAP | HCAP | core. 1 | core. 2 | core. 3 | Side chain | | |
| 6.1 | IT 20° C. Addition over 38 min. | 1.3 | 13.32 | — | 2 | 49.3 | 19.8 | 0.9 | 28.4 | 0.3 | 0.2 | | 18.4 |
| 6.2 | IT 50° C. Addition over 3 h | 1.3 | 13.3 | — | 2 | 41.1 | 21.4 | 2.5 | 0.3 | 2.8 | 10.2 | | 19.2 |

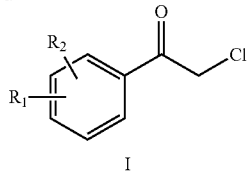

This solves the problem of chlorinated solvents like dichloromethane in the reaction. It further results in better quality of the reaction product in terms of side products in the isolated chlorinated product. It further allows using an aliphatic alcohol as moderator in an amount of less than equimolar amount, which also solves the problem of reducing the amount of chlorinated hydrocarbons in the reaction mixture and the waste products.

In a further embodiment of the invention, the reaction is performed in the presence of toluene and in the presence of an aliphatic alcohol in the amount of less than 1 molar equivalent compared to the substituted acetophenone used.

In a further embodiment of the invention, the reaction is performed in the presence of toluene and in the presence of an aliphatic alcohol in the amount of 0.1 to less than 1 molar equivalent compared to the substituted acetophenone used.

In a further embodiment of the invention, the reaction is performed in the presence of toluene and in the presence of an aliphatic alcohol in the amount of 0.1 to 0.5 molar equivalent compared to the substituted acetophenone used.

In a further embodiment of the invention, the reaction is performed in the presence of toluene and in the presence of an aliphatic alcohol in the amount of 0.1 to 0.3 molar equivalent compared to the substituted acetophenone used.

In a further embodiment of the invention, the reaction is performed in the presence of toluene and in the presence of an aliphatic alcohol in the amount of 0.2 molar equivalent compared to the substituted acetophenone used.

In a further embodiment of the invention, the reaction is performed in the presence of toluene and in the presence of a moderator selected from methanol, ethanol, n-propanol and n-butanol in the amount of less than 1 molar equivalent compared to the substituted acetophenone used.

In a further embodiment of the invention, the reaction is performed in the presence of toluene and in the presence of a moderator selected from methanol, ethanol, n-propanol and n-butanol in the amount of 0.1 to less than 1 molar equivalent compared to the substituted acetophenone used.

In a further embodiment of the invention, the reaction is performed in the presence of toluene and in the presence of a moderator selected from methanol, ethanol, n-propanol and n-butanol in the amount of 0.1 to 0.5 molar equivalent compared to the substituted acetophenone used.

In a further embodiment of the invention, the reaction is performed in the presence of toluene and in the presence of a moderator selected from methanol, ethanol, n-propanol and n-butanol in the amount of 0.1 to 0.3 molar equivalent compared to the substituted acetophenone used.

In a further embodiment of the invention, the reaction is performed in the presence of toluene and in the presence of a moderator selected from methanol, ethanol, n-propanol and n-butanol in the amount of 0.2 molar equivalent compared to the substituted acetophenone used.

In a further embodiment of the invention, the reaction is performed in the presence of toluene as the solvent and in the presence of a moderator selected from methanol and n-butanol in the amount of less than 1 molar equivalent compared to the substituted acetophenone used.

In a further embodiment of the invention, the reaction is performed in the presence of toluene as the solvent and in the presence of a moderator selected from methanol and n-butanol in the amount of 0.1 to less than 1 molar equivalent compared to the substituted acetophenone used.

In a further embodiment of the invention, the reaction is performed in the presence of toluene as the solvent and in the presence of a moderator selected from methanol and n-butanol in the amount of 0.1 to 0.5 molar equivalent compared to the substituted acetophenone used.

In a further embodiment of the invention, the reaction is performed in the presence of toluene as the solvent and in the presence of a moderator selected from methanol and n-butanol in the amount of 0.1 to 0.3 molar equivalent compared to the substituted acetophenone used.

In a further embodiment of the invention, the reaction is performed in the presence of toluene as the solvent and in the presence of a moderator selected from methanol and n-butanol in the amount of 0.2 molar equivalent compared to the substituted acetophenone used.

In a further embodiment of the invention, the reaction is performed in the presence of toluene as the solvent and in the presence of methanol as a moderator in the amount of less than 1 molar equivalent compared to the substituted acetophenone used.

In a further embodiment of the invention, the reaction is performed in the presence of toluene as the solvent and in the presence of methanol as a moderator in the amount of 0.1 to less than 1 molar equivalent compared to the substituted acetophenone used.

In a further embodiment of the invention, the reaction is performed in the presence of toluene as the solvent and in the presence of methanol as a moderator in the amount of 0.1 to 0.5 molar equivalent compared to the substituted acetophenone used.

In a further embodiment of the invention, the reaction is performed in the presence of toluene as the solvent and in the presence of methanol as a moderator in the amount of 0.1 to 0.3 molar equivalent compared to the substituted acetophenone used.

In a further embodiment of the invention, the reaction is performed in the presence of toluene as the solvent and in the presence of methanol as a moderator in the amount of 0.2 molar equivalent compared to the substituted acetophenone used.

The chlorinated acetophenone as produced by the before mentioned embodiments may be used for the manufacture of active pharmaceutical ingredients. For example it may be used for the synthesis of ephedrine:

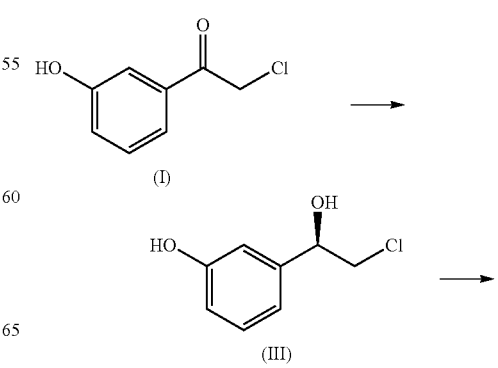

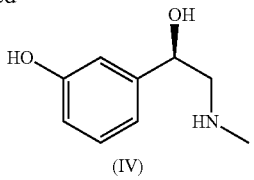

(IV)

With employing the new way of manufacture of compound (I) in the synthesis of ephedrine, no need of purification in the last step is necessary. Due to the low impurity content of compound (I) when manufactured by the process as described and claimed in this invention, the entire process is more efficient, more cost effective and produces less chlorinated volatile impurities in the process.

EXAMPLES

Wherever the unit of a measurement is characterized as "HPLC-result" or "area %" or "a %", the result of a H PLC-analysis of a solution in isopropanol is stated.

The value "Yield" refers to the isolated material. The H PLC-analysis shows the quality of the reaction product.

Where the amount of solvent is stated in volumes (vol), it is the volume in ml calculated on the starting material in g. 60 g Hydroxyacetophenone in 120 ml toluene is equivalent to a toluene volume of 2.

Where equivalents are given, the equivalents are molar equivalents calculated on the starting material.

IT means inner reactor temperature. JT means jacket temperature.

Example 1

Compatibility testing of solvents with sulfuryl chloride
60 ml of the solvent is stirred and sulfuryl chloride is added. The solution is monitored visually and the temperature is checked continuously. Results see Table 9

Example 2

Solubility of the Starting Material in the Solvent
To 1 g of HAP is added 5 ml of solvent. The mixture is stirred in a water bath at 20° C. The solvent is further slowly added under stirring until a clear solution appears.
The amount of used solvent is noted.

Example 3 (Comparative Example)

General procedure for the chlorination of 3-hydroxyacetophenon in dichloromethane 450 g of 3-hydroxyacetophenone are mixed with 1 l dichloromethane and 400 ml methanol. The mixture is cooled to 5-15° C.

While stirring 300 g of sulfuryl chloride are added within approx. 2 h, the temperature is kept between 10 to 15° C. A second portion of 300 g of sulfuryl chloride is added within approx. 2 h, the temperature is allowed to rise up to 17-22° C. After addition the mixture is stirred at least 30 minutes at 17-22° C. 50 ml water are added within approx. 1 h. The temperature is kept between 20 to 30° C. 75 ml water are added within approx. 3 h. The temperature is kept between 20 to 30° C. The layers are separated. The aqueous layer is washed with dichloromethane.

The organic layers are combined. The extract aqueous layer is disposed off.

Dichloromethane is distilled off from the organic layer at a maximum of 65° C. until the distillation stagnates. The pressure is reduced for further concentration. The distillate from the concentration is distilled again and may be reused.
Quality of HCAP solution in 2-propanol is as follows:

| | |
|---|---|
| 3-Hydroxyacetophenon | 1-3 area % |
| 2-Chlor-1-(2-chlor-3-hydroxyphenyl)-ethanone | 1-2 area % |
| 2-Chlor-1-(3-hydroxy-4-chlor-phenyl)-ethanone | 1-2 area % |
| 2-Chlor-1-(2-chlor-5-hydroxyphenyl)-ethanone | 2-4 area % |
| 2,2-Dichlor-1-(3-hydroxyphenyl)-ethanone | 4-6 area % |
| 2-Chlor-1-(3-hydroxyphenyl)-ethanone | 85-90 area % |

Example 4

General Procedure for the Chlorination of 3-Hydroxyacetophenone (HAP)
The results of different experiments are shown in Table 5 and Table 6. If changes to the general procedure were made, this also is disclosed in the tables. This might be with regards to the solvent volume for HAP, the solvent volume as diluent for sulfuryl chloride, the alcohol volume, the temperature, the equivalents of sulfuryl chloride or the addition time of the sulfuryl chloride.

11.3 g HAP is dissolved in the solvent mixture (6 vol of the solvent and 2 vol of the aliphatic alcohol) and the mixture is kept at 18° C. 15 g $SO_2Cl_2$ is added to the mixture under stirring over a period of 30 minutes keeping a temperature of between 18 and 23° C.

The mixture is stirred for another 60 minutes and 50 ml water is added. The organic phase is separated and analyzed.

Example 5

General Procedure for the Chlorination of 3-Hydroxyacetophenone in Toluene and n-Butanol
The results of different experiments are shown in Table 7 and Table 10. If changes to the general procedure were made, this also is disclosed in the tables. This might be with regards to the toluene volume for HAP, the toluene volume as diluent for sulfuryl chloride, the butanol volume, the temperature, the equivalents of sulfuryl chloride or the addition time of the sulfuryl chloride.

10.0 g of HAP (0.073 mol), 5.48 g (1 eq.) of n-Butanol and 17.4 g of toluene are charged to the jacketed reactor under nitrogen. The mixture temperature is kept with jacket temperature (JT) 20° C. Subsequently, 13.3 g sulfuryl dichloride (1.3 eq.), dissolved in 13.3 g (1 Vol) of toluene is added dropwise over 30 minutes, keeping the IT at 20° C. After addition of the sulfuryl chloride, the mixture is stirred for 60 minutes at IT 20° C. Afterwards, the suspension is cooled to IT 0-5° C. within ca. 20 minutes and stirred at this temperature for ca. 60 minutes. The product is filtered and washed with 20 ml toluene in 2 portions. The filter cake is dried over night at 40° C.

Example 6

General Procedure for the Chlorination of 3-Hydroxyacetophenon in Toluene without Moderator
10.01 g of HAP (0.073 mol), 17.40 g of toluene are charged to the jacketed reactor under nitrogen. The mixture is warmed up. Subsequently, 13.30 g sulfuryl dichloride (1.3 eq.), dissolved in 13.3 g (1 Vol) of toluene is added dropwise over 38 minutes, keeping the IT at 20° C. After addition of the sulfuryl chloride, the mixture is stirred for 60 minutes at IT 20° C.

The solvents are distilled off and the product is washed with 20 ml toluene in 2 portions. The filter cake is dried over night at 40° C.

Example 7

The results of different experiments are shown in Table 11. If changes to the general procedure were made, this also is disclosed in the table. This might be with regards to the toluene volume for HAP, the toluene volume as diluent for sulfuryl chloride, the methanol volume, the temperature, the equivalents of sulfuryl chloride or the addition time of the sulfuryl chloride.

General procedure for the chlorination of 3-Hydroxyacetophenon in toluene and methanol 60.0 g of HAP (0.441 mol), 1.4 g (0.1 eq.) of methanol and 105.0 g of toluene (120 mL-2 Vol) are charged to the jacketed reactor under nitrogen. The mixture is warmed up with jacket temperature (JT) 40° C. Subsequently, 1.4 g (0.1 eq.) of methanol, dissolved in 26.2 g (0.5 Vol) of toluene, and 71.4 g of sulfuryl dichloride (1.17 eq.), dissolved in 70.6 g of toluene are added in parallel within ca. 70 minutes. At ca. 80% of the sulfuryl dichloride addition the gas flow increases and inner temperature (IT) is rising to 42° C. The mixture is stirred for 60 minutes at IT 40° C. Afterwards, the suspension is cooled to IT 20-25° C. within 20 minutes. The sandy suspension is stirred for 30 minutes, then cooled to IT 0-5° C. within ca. 20 minutes and stirred at this temperature for ca. 4 hours. The product is filtered and washed with 104.5 g toluene in 2 portions. The filter cake is dissolved with 140.3 g of isopropanol and the filter is rinsed with 20 g of isopropanol. The isopropanol is distilled of and the product is dried over night at 40° C.

TABLE 9

| Minutes | DCM T [° C.] | Tetraglyme T [° C.] | THF T [° C.] | Ether T [° C.] | p-dioxane T [° C.] | Methanol T [° C.] | Ethanol T [° C.] | Acetone T [° C.] | Acetonitrile T [° C.] |
|---|---|---|---|---|---|---|---|---|---|
| 0 | 18 | 18 | 18 | 20 | 20 | 20 | 20.5 | 20.5 | 19 |
| 1 | 18 | 18 | 24 | 20 | | 24 | 22 | 23.5 | 19 |
| 4 | 18.5 | 20 | 34 | 20 | 32 | 28 | 29 | 32 | 19 |
| 7 | 18.5 | 22 | | 20.5 | | | | | 19 |
| 12 | 19 | 24 | | 21 | | | | | 19 |
| 15 | 19 | 24 | | 21.5 | | | | | 19 |
| 20 | 19 | 25 | | 22.5 | | | | | 19 |
| 25 | 19 | 25 | | 22.5 | | | | | 19 |
| 28 | 19.5 | 25.5 | | 23 | | | | | 19 |
| 31 | 19.5 | 25 | | 23 | | | | | 19 |
| 34 | 19.5 | 25 | | 23.5 | | | | | 19 |
| 45 | 19.5 | 25 | | 24 | | | | | 19 |
| observations | None | Slight gaseous evolution, green yellowish color. | Drastic gas evolution and increasing temperatue | Slight gaseous evolution | Drastic gas evolution and increasing temperatue | Drastic gas evolution and increasing temperatue | Drastic gas evolution and increasing temperatue | Drastic gas evolution and increasing temperatue | Yellowish immediately |

TABLE 10

| | | Volumes | | | | HPLC-results [a %] | | | | | |
|---|---|---|---|---|---|---|---|---|---|---|---|
| Example | Remarks* | SO$_2$Cl$_2$ [eq.] | Toluene (dil. of SO$_2$Cl$_2$) [g] | n-Butanol [eq.] | Toluene [Vol] | 3-HAP | HCAP | core. 1 | core. 2 | core. 3 | Side Chain | yield [%] |
| 5.8 | | 1.3 | n.a. | 2 | 2 | 3.5 | 89.8 | 0.4 | 0.4 | 0.7 | 1.8 | 48.6 |
| 5.9 | | 1.3 | 13.36 | 1.5 | 2 | 0.7 | 98.6 | <0.05 | 0.2 | 0.2 | 0.3 | 65.3 |
| 5.10 | | 1.3 | 13.3 | 1.0 | 2 | 2.0 | 97.5 | <0.05 | 0.1 | 0.1 | 0.2 | 68.9 |
| 5.11 | IT 20° C. | 1.3 | 13.28 | 0.5 | 2 | 2.5 | 96.5 | <0.05 | 0.2 | 0.3 | 0.5 | 68.8 |
| 5.12 | IT 20° C. | 1.3 | 13.31 | 0.1 | 2 | 2.5 | 96.5 | <0.05 | 0.2 | 0.3 | 0.5 | 69.3 |
| 5.13 | IT 10° C. | 1.3 | 13.29 | 0.1 | 2 | 1.5 | 97.7 | <0.05 | 0.15 | 0.26 | 0.33 | 65.4 |
| 5.14 | IT 30° C. | 1.3 | 13.29 | 0.1 | 2 | 2.34 | 96.95 | <0.05 | 0.09 | 0.21 | 0.42 | 68.9 |
| 5.15 | IT 40° C. | 1.3 | 13.33 | 0.1 | 2 | 0.07 | 98.22 | n.d. | 0.17 | 0.72 | 0.82 | 61.5 |
| 5.16 | IT 30° C. Addition over 3 hr | 1.3 | 13.29 | 0.1 | 2 | 1.33 | 97.65 | n.d. | 0.10 | 0.35 | 0.56 | 67.4 |

TABLE 10-continued

| | | | Volumes | | | HPLC-results [a %] | | | | | | |
|---|---|---|---|---|---|---|---|---|---|---|---|---|
| Example | Remarks* | $SO_2Cl_2$ [eq.] | Toluene (dil. of $SO_2Cl_2$) [g] | n-Butanol [eq.] | Toluene [Vol] | 3-HAP | HCAP | core. 1 | core. 2 | core. 3 | Side Chain | yield [%] |
| 5.17 | IT 20-30° C. | 1.3 | 13.28 | 0.25 | 2 | 2.37 | 96.99 | n.d. | 0.10 | 0.15 | 0.39 | 70.8 |
| 5.18 | IT 30° C. Addition over 3 h | 1.15 | 11.42 | 0.1 | 2 | 1.52 | 97.09 | 0.02 | 0.17 | 0.55 | 0.65 | 61.0 |
| 5.19 | IT 40° C. Addition over 3 h | 1.15 | 11.45 | 0.1 | 2 | 1.38 | 97.56 | 0.04 | 0.11 | 0.24 | 0.44 | 70.4 |
| 5.20 | IT 30° C. Addition over 3 h | 1.15 | 11.44 | 0.2 | 2 | 2.03 | 97.56 | n.d. | 0.07 | 0.16 | 0.18 | 73.9 |
| 5.21 | IT 30° C. Addition over 0.5 h | 1.15 | 11.4 | 0.2 | 2 | 2.19 | 97.34 | n.d. | 0.07 | 0.16 | 0.24 | 78.2 |
| 5.22 | IT 30° C. | 1.15 | 11.44 | 0.2 | 3 | 1.81 | 97.61 | n.d. | 0.08 | 0.21 | 0.30 | 74.5 |

*Remarks contain differences to the standard procedure

| | | | Volumes | | | HPLC-results [a %] | | | | | | | | |
|---|---|---|---|---|---|---|---|---|---|---|---|---|---|---|
| Example | Remarks* | $SO_2Cl_2$ [eq.] | Toluene (dil. of $SO_2Cl_2$) [g] | Methanol [eq.] | Toluene [Vol] | 3-HAP | RRT 0.92 | HCAP | RRT 1.01 | core. 1 | core. 2 | core. 3 | side-chain | RRT 1.30 | yield [%] |
| 7.1 | IT 10-12 °C. | 1.15 | 35.3 | 0.2 | 2 | 6.4 | 0.4 | 73.6 | n.d. | 3.4 | 0.4 | 3.5 | 1.7 | 0.3 | 62.2 |
| 7.2 | IT 19-22 °C. | 1.15 | 35.3 | 0.2 | 2.5 | 0.63 | n.d. | 98.18 | n.d. | n.d. | 0.10 | 0.32 | 0.63 | 0.08 | 78.5 |
| 7.3 | IT 30-34 °C. | 1.16 | — | 0.2 | 2.5 | 0.3 | n.d. | 98.4 | n.d. | n.d. | 0.1 | 0.3 | 0.8 | n.d. | 74 |
| 7.4 | IT 35-37 °C. | 1.16 | | 0.2 | 2.5 | 2.1 | n.d. | 97.1 | n.d. | n.d. | 0.1 | 0.1 | 0.2 | 0.1 | 80.1 |
| 7.5 | IT 38-42 °C. | 1.17 | | 0.2 | 2.5 | 2.0 | n.d. | 97.5 | n.d. | 0.1 | 0.1 | 0.2 | 0.8 | 0.1 | 78.4 |
| 7.6 | IT 38-42 °C. | 1.06 | | 0.2 | 2.5 | 2.9 | n.d. | 95.5 | n.d. | 0.1 | 0.1 | 0.3 | 0.9 | 0.1 | 82 |
| 7.7 | IT 38-42 °C. | 1.1 | | 0.2 | 2.5 | 1.7 | n.d. | 97.8 | n.d. | 0.1 | 0.1 | 0.2 | 0.1 | | 82 |
| 7.8 | IT 38-42 °C. | 1.17 | | 0.2 | 2.5 | 1.54 | n.d. | 97.81 | n.d. | n.d. | 0.07 | 0.15 | 0.12 | n.d. | 80 |
| 7.9 | IT 38-42 °C. | 1.15 | | 0.2 | 2.5 | 1.8 | n.d. | 98.0 | n.d. | n.d. | 0.05 | 0.08 | 0.08 | n.d. | 81 |
| 7.10 | IT 38-42 °C. | 1.15 | | 0.2 | 2.5 | 1.8 | n.d. | 98.0 | n.d. | n.d. | 0.04 | 0.08 | 0.12 | n.d. | 82 |

*Remarks contain differences to the standard procedure

The invention claimed is:

1. A process for manufacturing a compound of formula (I)

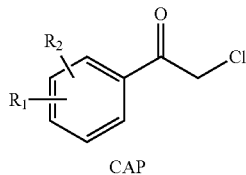

CAP wherein a compound of formula II is chlorinated with sulfuryl chloride to form the compound of formula I according to the following scheme:

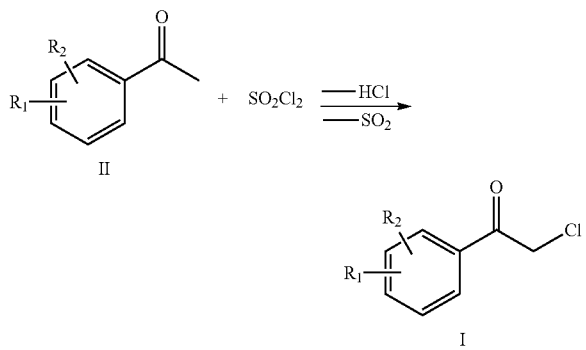

wherein $R_1$ and $R_2$ are independently H or OH or a substituted C1-C4 alkyl, and wherein the reaction is conducted in the presence of toluene at a temperature higher than 20° C.

2. A process according to claim 1, wherein $R_1$ is 3-OH and $R_2$ is H, so that the compound of formula II is 3-hydroxy-acetophenone.

3. A process according to claim 1, wherein the reaction furthermore comprises the presence of an aliphatic alcohol.

4. A process according to claim 3, wherein the aliphatic alcohol is selected from methanol, ethanol, 1-propanol, and 1-butanol.

5. A process according to claim 3, wherein the aliphatic alcohol is methanol.

6. A process according to claim 3, wherein the aliphatic alcohol is present in an amount of less than 1.0 molar equivalents compared to formula (II).

7. A process according to claim 3, wherein the amount of the aliphatic alcohol is from 0.1 to 0.5 molar equivalents compared to formula (II).

8. A process according to claim 3, wherein the amount of the aliphatic alcohol is 0.2 molar equivalents compared to formula (II).

9. A process according to claim 1 wherein the temperature is more than 30° C.

10. A process according to claim 9, wherein the temperature is between 38° C. and 42° C.

11. A process for the preparation of ephedrine comprising:
preparation of 3-hydroxychloroacetopheoneone (I) with $R_1$=H and $R_2$=3-OH according to claim 1;
asymmetric reduction of the carbonyl functionality to the respective alcohol (III), and
conversion of the chloride to the methylamine to form ephedrine (IV)

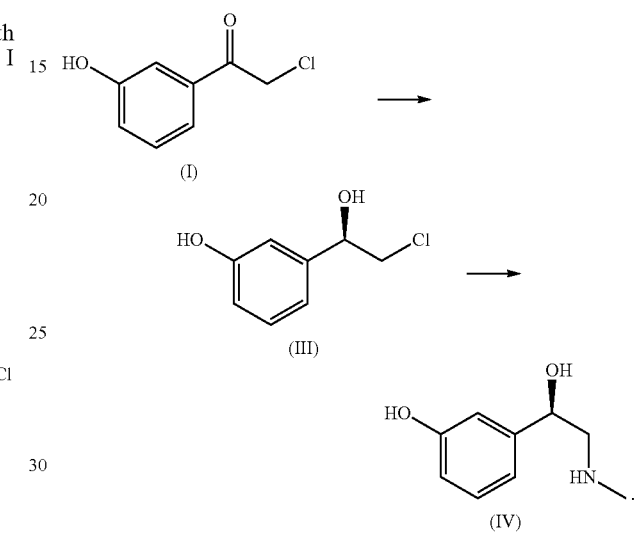

12. A process according to claim 2, wherein the reaction furthermore comprises the presence of an aliphatic alcohol.

13. A process according to claim 12, wherein the aliphatic alcohol is selected from methanol, ethanol, 1-propanol, and 1-butanol.

14. A process according to claim 13, wherein the aliphatic alcohol is methanol.

15. A process according to claim 12, wherein the aliphatic alcohol is present in an amount of less than 1.0 molar equivalents compared to formula (II).

16. A process according to claim 15, wherein the amount of the aliphatic alcohol is from 0.1 to 0.5 molar equivalents compared to formula (II).

17. A process according to claim 16, wherein the amount of the aliphatic alcohol is 0.2 molar equivalents compared to formula (II).

18. A process according to claim 2, wherein the temperature is more than 30° C.

19. A process according to claim 18, wherein the temperature is between 38° C. and 42° C.

* * * * *